United States Patent [19]

Hermans

[11] Patent Number: 4,802,825

[45] Date of Patent: Feb. 7, 1988

[54] METHOD AND APPARATUS FOR MAINTAINING A MIXTURE OF PRODUCTS AT A CERTAIN TEMPERATURE

[75] Inventor: Willem F. Hermans, Amstelveen, Netherlands

[73] Assignee: Stork Amsterdam B.V., Amsterdam, Netherlands

[21] Appl. No.: 49,617

[22] Filed: May 13, 1987

[30] Foreign Application Priority Data

May 14, 1986 [NL] Netherlands .......................... 8601221

[51] Int. Cl.$^4$ ............................................. F04D 29/38
[52] U.S. Cl. ............................ 416/231 B; 416/277 R; 366/328
[58] Field of Search ........... 416/231 R, 231 A, 231 B, 416/227 A, 227 R; 366/144, 279, 325, 326, 328; 99/485

[56] References Cited

U.S. PATENT DOCUMENTS

| | | | |
|---|---|---|---|
| 1,525,394 | 2/1925 | Jolicoeur | 366/328 |
| 2,448,849 | 9/1948 | Wagner et al. | 366/326 |
| 2,805,843 | 9/1957 | Block | 366/326 |
| 3,130,694 | 4/1964 | Gatzke | 416/227 |
| 4,162,128 | 7/1979 | Ogden et al. | 366/328 |
| 4,192,615 | 3/1980 | Fortunski et al. | 366/328 |
| 4,401,606 | 8/1983 | Matsuoka | 366/325 |

Primary Examiner—Robert E. Garrett
Assistant Examiner—John T. Kwon
Attorney, Agent, or Firm—Arnold S. Weintraub

[57] ABSTRACT

When maintaining a flow of a mixture of products consisting of a liquid of low to medium viscosity incorporating solid particles at a certain temperature and for a certain period of time the mixture remains for some time in a vessel of a substantially cylindrical shape. The residence time in the vessel of the solid particles mixed with the liquid is controlled separately from the liquid in that the solid particles are carried through the vessel at a regulable speed, independently of the speed of flow of the liquid through the vessel, with the aid of a rotatable conveyor means which is permeable to liquid but not to the solid particles and whose axis of rotation coincides with the axis of the vessel. The solid particles remain mixed with the liquid. The residence time of the solid particles is regulated such that the core of the solid particles attains the same temperature as the liquid, without the liquid remaining for too long a time at the desired end temperature.

2 Claims, 2 Drawing Sheets

METHOD AND APPARATUS FOR MAINTAINING A MIXTURE OF PRODUCTS AT A CERTAIN TEMPERATURE

BACKGROUND OF THE INVENTION

The invention relates to a method and an apparatus for maintaining at a certain temperature, and for a certain period of time, a flow of a mixture of products consisting of a liquid of low to medium viscosity incorporating solid particles.

In continuous flow heating or cooling by means of heat exchangers (for example a tubular heat exchanger) of liquids of low to medium viscosity in which a certain volume percentage of solid particles is contained (for example a soup containing pieces of vegetables and meat), the transfer of heat is effected from the wall of the heat exchanger via the flowing liquid, the flow of which may or may not be turbulent, to the outer edge of the solid particles, and thence to the core of the latter. With this type of heat transfer the conveying liquid will have reached the desired final temperature far more quickly than the core of the solid particles entrained by the liquid. If for technical reasons connected with the process it is necessary for the core of the solid particles also to attain the same temperature as the liquid, the liquid and the solid particles must be kept at a constant end temperature for so long a time that differences in temperature between the liquid and the core of the solid particles are eliminated. This may have the consequence that the liquid remains for too long a time at the desired end temperature, so that (for example in the case of a food product) undesirable changes of taste and colour occur.

It is possible to subject the liquid and the solid particles separately to the desired heat treatment and to mix the two components together only after completion of the process or during the course of the latter. However, this necessitates two heat treatment installations in parallel, while in particular the plant required for the heat treatment of the solid particles is relatively complicated.

SUMMARY OF THE INVENTION

The present invention now seeks to provide a method and an apparatus in which the core of the solid particles attains practically the same temperature as the liquid, without the liquid remaining for an undesirably long period of time at a certain temperature and without the solid particles being separated from the liquid for the purpose of undergoing separate heat treatment.

This aim is achieved through a method of the kind described in the preamble, in which the mixture remains for some time in a vessel, which method is characterized in that the residence time in the vessel of the solid particles mixed with the liquid is separately controlled.

It is thus possible to ensure that the residence time in the vessel of the liquid and that of the solid particles mixed with the liquid are different and can be controlled in such a manner that the liquid does not remain too long at a certain end temperature, while the solid particles remain sufficiently long in the liquid to ensure that the core of the fixed particles attain substantially the same temperature as the liquid.

The solid particles are preferably carried through the vessel at a regulable speed with the aid of a conveyor means, independently of the speed of flow of the liquid through the vessel, while the solid particles remain mixed with the liquid.

In this way it is very simple to control the residence time in the vessel of the solid particles mixed with the liquid.

The apparatus for applying the method according to the invention comprises a vessel in which the mixture of products remains for some time and to which mixture inlet and outlet pipes are connected, and it is characterized in that a conveyor mechanism acting selectively on the solid particles is mounted in the vessel, whereby the conveying speed and consequently the residence time of the solid particles in the vessel can be controlled.

The vessel is preferably substantially cylindrical in shape and the conveyor mechanism preferably comprises a conveyor means which is rotatable at a variable speed and whose axis of rotation coincides with the axis of the cylindrical vessel, while it i provided with at least one conveyor element permeable to liquid.

Because of this arrangement, on the one hand the liquid can flow freely through the vessel, while on the other hand the solid particles contained in the liquid can in a simple manner be carried at a certain speed through the vessel, the conveying speed being adjustable by regulating the speed of rotation of the conveyor means.

In a specific embodiment of the apparatus according to the invention the conveyor element permeable to liquid is situated in a surface extending from the axis of rotation in the outward direction and lying parallel to the axis of rotation of the conveyor means, and the free peripheral edge of the conveyor member is situated near the inner side of the cylindrical peripheral wall and the end walls of the vessel. In this arrangement the conveyor element may be disposed in either a flat plane or a curved surface.

In order to make the conveyor element permeable to liquid, it has a sieve-like structure or is provided with slots. In a practical embodiment of the apparatus according to the invention the conveyor element consists of a plurality of pins extending perpendicularly outwards from the axis of rotation of the conveyor means and spaced apart from each other in the direction of said axis, with their ends situated near the inner side of the cylindrical wall of the vessel.

At the site of the outlet pipe for the mixture an element may be installed in the vessel for the purpose of removing the solid particles from the conveyor member, which element consists of a series of pins disposed next to one another and spaced apart in the longitudinal direction of the vessel, which pins extend from the cylindrical wall of the vessel towards the axis of rotation of the conveyor means and engage between the pins of the conveyor element.

In this way it is ensured that at the site of the outlet pipe the particles will be removed from the conveyor element and will then be discharged by means of the liquid flowing through the vessel.

The invention will now be explained by means of a description of two preferred embodiments of the invention and with reference to the drawings.

DETAILED DESCRIPTION OF THE PREFERRED EMBODIMENTS

The apparatus according to the invention is intended to form part of a heat treatment installation in which a liquid and solid particles contained therein undergo a certain heat treatment. The apparatus according to the invention is therefore also referred to s a unit for keeping hot.

Figure 1:
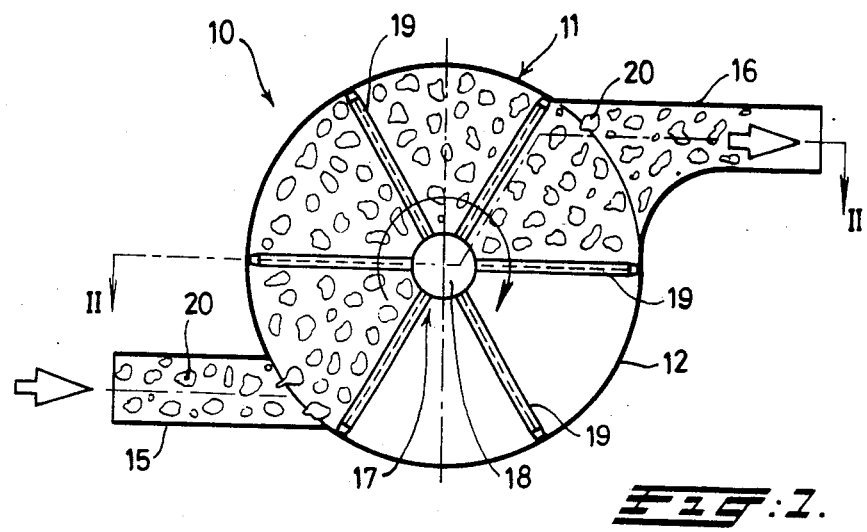
FIG. 1 shows schematically an embodiment of an apparatus according to the invention in a section perpendicular to the axis of rotation of the conveyor member.
Figure 2:
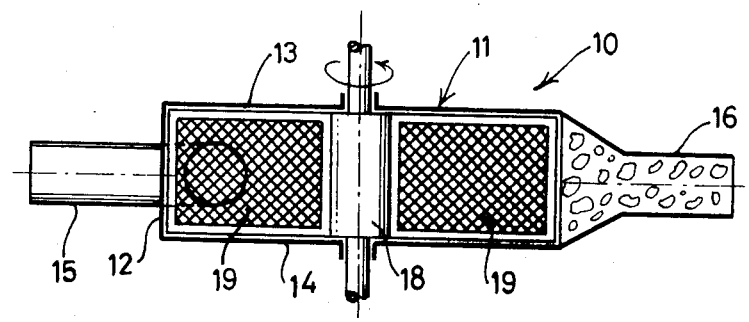
FIG. 2 is a section of the apparatus shown in FIG. 1, taken on the line II—II.

The embodiment of the apparatus shown in FIGS. 1 and 2 is given the general designation 10 and comprises a substantially closed cylindrical vessel 11 having a peripheral wall 12 and two end walls 13 and 14. An inlet pipe 15 and an outlet pipe 16 are connected to the peripheral wall.

A rotating bladed wheel 17 is mounted inside the vessel 11 and consists of a shaft 18 on which blades 19, of which in the present case there are six, are mounted. The axis of rotation of the bladed wheel coincides with the axis of the cylindrical vessel 11. The free peripheral wall of each of the blades 19 is situated near the inner side of the cylindrical peripheral wall 12 and the two end walls 13 and 14 of the vessel 11. The blades 19 are permeable to liquid, and for this purpose, as shown in FIG. 2, have a sieve-like structure. It is however also possible for the blades 19 to be provided with slots.

The bladed wheel 17 can be driven at an adjustable speed of rotation by means of a shaft passing through one or both end walls 13, 14. The drive means is not shown in the drawings.

The mixture which has to be kept at a certain temperature for a certain period of time, and which consists of a liquid of low to medium viscosity and of solid particles contained therein, can be fed via the inlet pipe 15 and discharged through the outlet pipe 16. The liquid can flow directly from the inlet pipe 15 via the opening in the blades, freely in all directions, through the vessel towards the outlet pipe 16. The liquid will for this purpose take the path of least resistance.

The solid particles 20 contained in the liquid will on the other hand be held back by the rotating blades 19 and thus prevented from taking the shortest route from the inlet pipe 15 to the outlet pipe 16. The solid particles are caught between the blades 19 of the driven bladed wheel and carried in the direction of rotation of the latter until they reach the outlet pipe 16. The solid particles 20 there leave the spaces between the blades 19, being entrained by the liquid flowing through the vessel 11, and reach the outlet pipe 16. Adjustment of the speed of rotation of the bladed wheel 17 enables the residence time of the solid particles 20 in the vessel 11 to be determined irrespective of the residence time of the liquid in the vessel. The residence time of the solid particles 20 in the vessel can be adjusted in such a manner that there is sufficient time for the core of the solid particles 20 to reach the same temperature as that of the liquid. In this way it is ensured that both the liquid and the solid particles in the mixture will have substantially the same temperature when they leave the apparatus via the outlet pipe 16.

Figure 3:
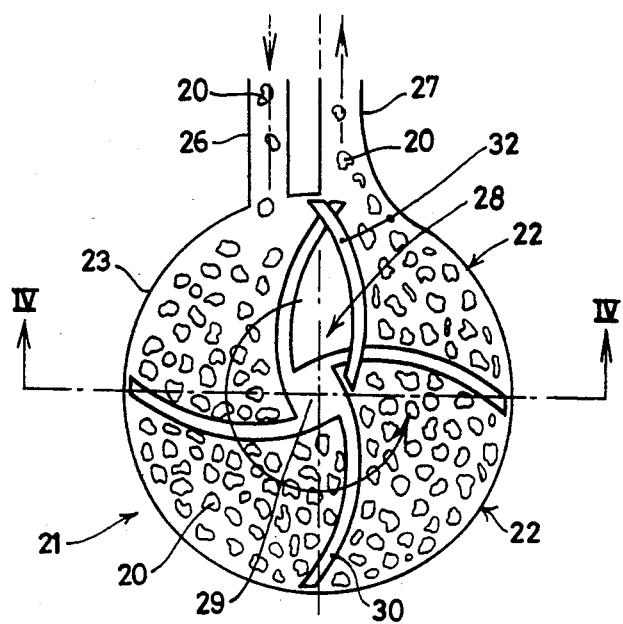
FIG. 3 shows schematically another embodiment of an apparatus according to the invention in a similar section to FIG. 1.
Figure 4:
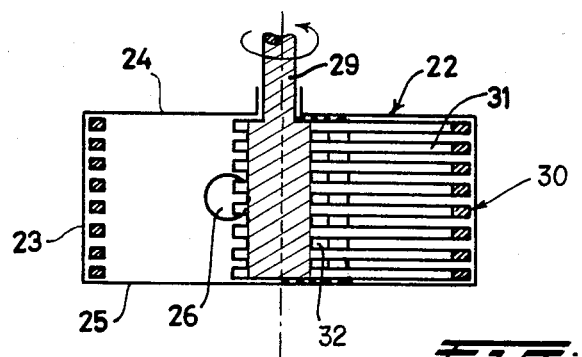
FIG. 4 is a section of the apparatus shown in FIG. 3, taken on the line IV—IV.

FIG. 3 and 4 show another embodiment of the apparatus according to the invention, which is given the general designation 21. The apparatus again comprises a substantially cylindrical vessel 22 having a cylindrical peripheral wall 23 and end walls 24 and 25. An inlet pipe 26 and an outlet pipe 27 are likewise connected to the vessel, the inlet pipe 26 and the outlet pipe 27 being situated rather differently from the arrangement shown in FIGS. 1 and 2. In this embodiment also use is made of a bladed wheel 28, which consists of blades 30, of which in this case there are four, mounted on a shaft 29.

Each blade 30 consists of a plurality of pins 31 extending outwards perpendicularly from the shaft 29 and spaced apart in the direction of the latter, their ends being situated near the inner side of the cylindrical wall 23 of the vessel 22. In the embodiment illustrated the pins 31 are curved. It is however also possible for the pins to be straight.

The operation of the apparatus shown in FIGS. 3 and 4 is identical to that of the apparatus shown in FIGS. 1 and 2.

Figure 5:
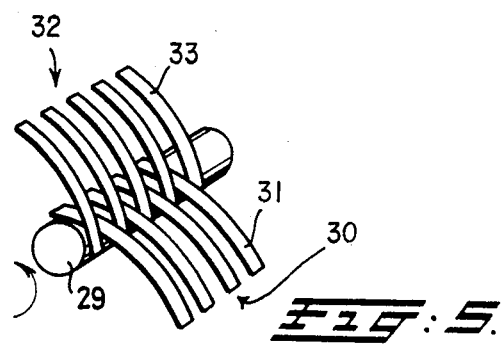
FIG. 5 shows schematically in perspective a conveyor element mounted on a shaft and consisting of pins, with an element engaging between them for removing the solid particles.

For the purpose of removing the solid particles 20 from the blades 30, there is provided in the vessel 22, at the site of the outlet pipe 27, an element 32 consisting of a series of pins 33, which are disposed next to one another and spaced apart in the longitudinal direction, and which extend from the cylindrical wall 23 of the vessel 22 towards the shaft 29 and engage between the pins 31 of the blades 30. It can thus be ensured that no solid particles will remain behind on the blades and thus be able to make a second passage around the vessel, in which case the residence time of these solid particles would exceed the maximum residence time. FIG. 5 shows schematically the shaft 29 with a blade 30, consisting of pins 31, mounted on it, together with the means 32 consisting of pins 33. Solid particles 20 which may have been jammed between the pins 31 are so-to-speak pushed by the pins 33 in the lengthwise direction of the pins 31, out of the slots formed between the latter.

With the apparatus according to the invention it is thus possible to control the residence time of the solid particles in a mixture consisting of a liquid of low to medium viscosity and solid particles contained therein, independently of the residence time of the liquid in the vessel, without the solid particles being separated from the liquid. It can thus be ensured that the solid particles will attain the desired end temperature even in their cores, without the liquid remaining too long at the end temperature, which in the case of foodstuffs, for example, could lead to undesirable changes of taste and colour.

What is claimed is:

1. A method of maintaining at a certain temperature, and for a certain period of time, a flow of a mixture of products consisting of a liquid of low to medium viscosity incorporating solid particles, wherein the residence time in the vessel of the solid particles mixed with the liquid is separately controlled, such that a desired temperature of the solids can be reached independent of the flow of the liquid.

2. A method as claimed in claim 1, wherein the solid particles are carried through the vessel at a regulable speed with the aid of conveyor means, independently of the speed of flow of the liquid through the vessel, while the solid particles remain mixed with the liquid.

* * * * *

UNITED STATES PATENT OFFICE
CERTIFICATE OF CORRECTION

Patent No. 4,802,825　　　　　　　Dated Feb. 7, 1989

Inventor(s) Willem F. Hermans

It is certified that error appears in the above-identified patent and that said Letters Patent is hereby corrected as shown below:

On the title page, under [45] Date of Patent, please change "1988" to --1989--.

Signed and Sealed this

Eighteenth Day of July, 1989

Attest:

DONALD J. QUIGG

Attesting Officer　　　　Commissioner of Patents and Trademarks